United States Patent

Knebelman

Patent Number: 4,718,850
Date of Patent: Jan. 12, 1988

[54] METHOD FOR DETERMINING VERTICAL DIMENSION

[76] Inventor: Stanley Knebelman, 20 Overbrook Pkwy., Overbrook Hills, Pa. 19151

[21] Appl. No.: 899,005

[22] Filed: Aug. 22, 1986

[51] Int. Cl.$^4$ .............................................. A61C 19/04
[52] U.S. Cl. ......................................... 433/72; 33/513
[58] Field of Search ...................... 433/72, 73, 68, 69; 33/511, 513, 514

[56] References Cited

U.S. PATENT DOCUMENTS

| 1,804,567 | 5/1931 | Pray | 433/72 |
| 2,125,809 | 8/1938 | Puckett | 433/72 |
| 2,491,136 | 12/1949 | Salzmann | 433/72 |
| 2,752,689 | 7/1956 | Adams | 33/513 |

FOREIGN PATENT DOCUMENTS 0309705  9/1969  U.S.S.R. ................................ 433/72

OTHER PUBLICATIONS

Coble, L. G., "Correct Jaw Relations by a New Technic", *Dental Survey*, Oct. 1938, pp. 1195-1196.

*Primary Examiner*—John J. Wilson
*Assistant Examiner*—Adriene J. Lepiane
*Attorney, Agent, or Firm*—Dann, Dorfman, Herrell and Skillman

[57] ABSTRACT

Vertical dimension of occlusion, i.e. the vertical dimension of the face with the posterior teeth fitting tightly together, is readily determined by a method comprising first measuring the distance between the external auditory meatus and the lateral corner of the occular orbit, making an adjustment in the first measurement to arrive at the factored distance and then positioning the mandible so that the distance between the nasal spine and the anterior part of the undersurface of the mandible corresponds to the factored distance. Gauging devices are disclosed for performing the method.

6 Claims, 5 Drawing Figures

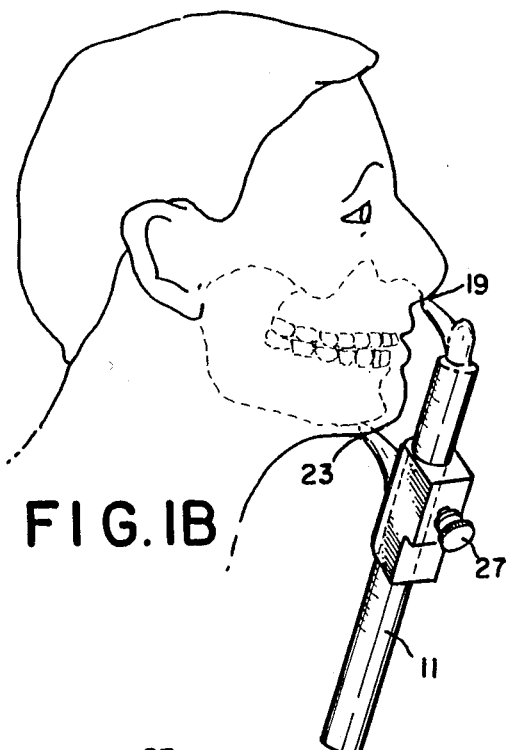
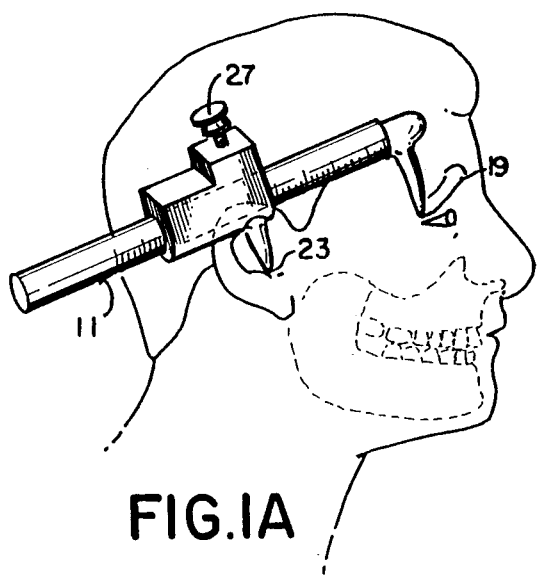
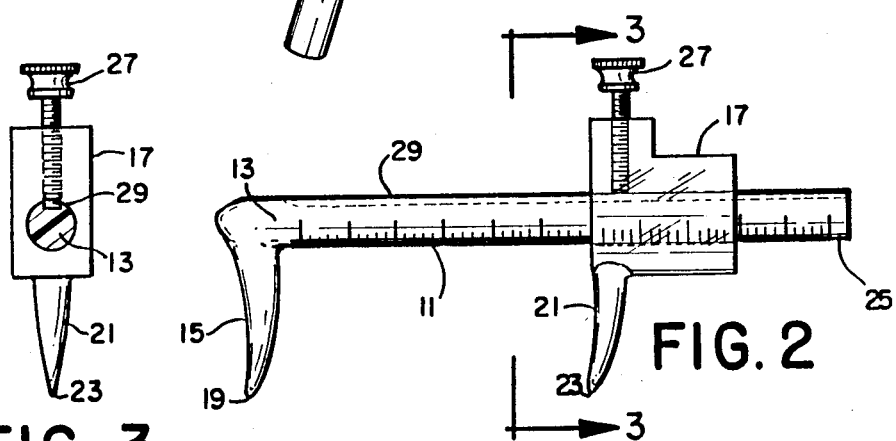
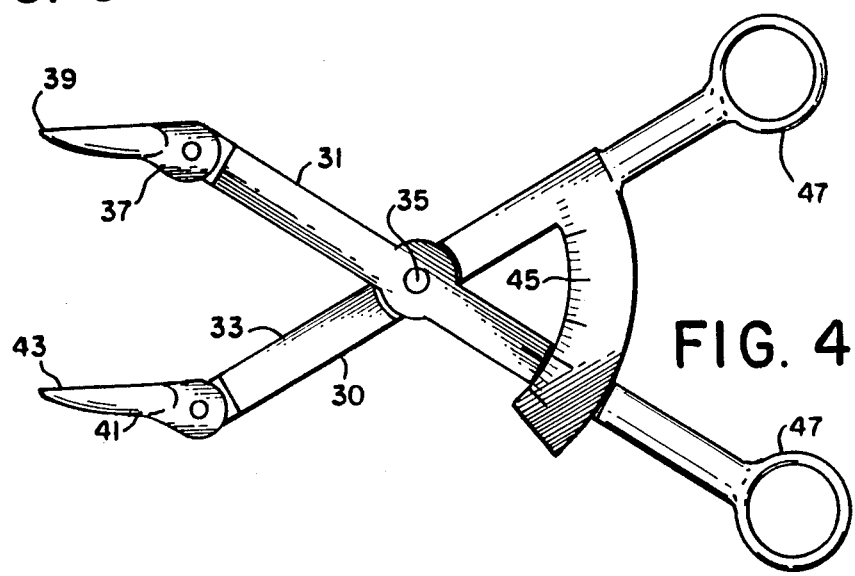

METHOD FOR DETERMINING VERTICAL DIMENSION

BACKGROUND OF THE INVENTION

The present invention relates to prosthodontics, and in particular to a method for facilitating dental restorations, such as the construction of complete dentures.

The accurate determination of the vertical jaw relation is extremely important in the fitting of dentures, as well as in other dental restoration work. Vertical relation, or vertical dimension refers to the degree of separation between the mandible, or lower jaw-bone and the maxillae, or upper jaw-bone. An appreciable increase or decrease in the vertical dimension of the mandible to the maxillae may cause problems in masticatory performance and speech. Deviations in vertical dimension may also cause temporomandibular joint disorders, which are often accompanied by severe physical discomfort in the jaw and neck regions. In certain cases, soreness of the supporting tissues may result, making the jaw region a target for rapid bone resorption.

In practice, the determination of the occlusal vertical dimension is the starting point for complete denture treatment. Occlusal vertical dimension is generally defined as the vertical dimension of the face when the teeth are in natural maximum contact in centric occlusion, i.e., with the posterior teeth fitting tightly together. Determination of the occlusal vertical dimension establishes the reference position from which all other horizontal jaw relation positions are recorded.

Many techniques have been proposed heretofore for facilitating the determination of occusal vertical dimension. Preextraction records, such as profile photographs, softwire profile silhouettes, occluded diagnostic casts, resin face masks and facial measurements have been found to be of value in many cases. Various instruments have been used for making facial measurements, including Sorenson's profile guide and the Willis device. More sophisticated approaches, such as radiographic techniques and electromyography have also been used. The Boos Bimeter, a device that measures the maximum force of jaw closure has been advocated by some clinicians and researchers. In addition, the patient's swallowing threshold, closest speaking space, phonetics, tactile sense, and parallelism of the ridges in the posterior region of the jaw have been used with varying degrees of success.

Although there are a number of different approaches in use, it is generally acknowledged by experienced prosthodontists that there is no precise scientific method of determining the correct occlusal vertical dimension. The acceptability of any vertical dimension determination depends largely upon the skill, experience and judgment of the prosthodontist. Thus, a need exists for a reliable method for accurately determining vertical dimension to facilitate dental restorations.

SUMMARY OF THE INVENTION

This invention provides a reliable method for accurately determining vertical dimension of occlusion, based on an anatomical correlation that has been found to exist between certain measurable craniofacial features. Specifically, it has been found that the distance between the horizontal axis of the condyles of the mandible and the zygomatic frontal suture line is generally equal to the distance between the nasal spine and the most anterior part of the sub-mental region of the mandible, when craniocervical spine posture is normal, and the upper and lower teeth are in natural or normal maximum contact in centric occlusion. Since the horizontal distance between the zygomatic frontal suture line and the bony lateral corner of the occular orbit generally corresponds to the distance between the horizontal axis of the condyles of the mandible and the anterior wall of the external auditory meatus, adjusted by a factored distance based on the relative size of the cranium, as will be described below, vertical dimension of occlusion can be readily determined simply by initially measuring the distance between the external auditory meatus and the lateral corner of the occular orbit, taking into account the factored distance to arrive at a final measurement and then positioning the mandible so that the distance between the nasal spine and the anterior part of the undersurface of the mandible corresponds to the final measurement.

The above-described method is performed using a gauging device comprising a first probe terminating in a first tip portion affording registry thereof with the above-noted anatomical features or parts and a second probe which is adjustably mounted substantially parallel to the first probe for adjustment relative to the first probe and which has a second tip portion affording registry of complementary anatomical features or parts therewith. In practicing the method of the invention, one of the tips of the gauging device is placed in registry with the external auditory meatus and the device is then adjusted to register the other of the tips with the lateral corner of the occular orbit to establish an initial measurement. The tip of the second probe is then positioned a factored distance relative to the tip of the first probe, based on the first measurement. Thereafter, and without changing the relative positions of the tips of the gauging device, one of the tips is placed in registry with the nasal spine and the other tip is positioned adjacent the anterior part of the undersurface of the mandible and the mandible is then positioned to engage the other tip. The gauging device is preferably provided with a scale to facilitate making the initial measurement and positioning the second probe to account for the factored distance.

The method of the invention has been found to provide accurate vertical dimension determinations in more than 95% of the cases in which it has been used.

BRIEF DESCRIPTION OF THE DRAWINGS

The novel features and advantages of the present invention are set forth more fully in the following description thereof, with reference to the accompanying drawings, in which:

FIG. 1A is a perspective illustration of a gauging device positioned to establish the initial measurement made in performing the method of the invention;

FIG. 1B is a perspective illustration of the gauging device positioned to establish proper vertical dimension of occlusion according to the method of the invention;

FIG. 2 is a side elevation of a preferred gauging device for performing the method of the invention;

FIG. 3 is a sectional view taken along line 3—3 of FIG. 2; and

FIG. 4 is an alternate embodiment of a gauging device for performing the method of the invention.

DETAILED DESCRIPTION OF THE INVENTION

Referring now to FIGS. 1–4 of the drawing, there is shown in FIG. 2 a preferred embodiment of a gauging device 11 for use in performing the method of the invention. This device comprises an enlongated rod-like body 13 having an elongated axis, with first probe 15 adjacent one end of the body projecting transversely from the axis and a slide 17 axially adjustable on the rod-like body. The second probe 21 is disposed on and projects from the slide substantially parallel to the first probe. A scale 25 is provided longitudinally on the rod-like body, which lies along the path of adjustment of the slide. Each probe has a tip portion 19, 23 adopted for registry with selected anatomical parts, including the external auditory meatus, the lateral corner of the occular orbit, the nasal spine and the most anterior part of the submental region of the mandible.

The rod-like body 13 and sleeve 17 are preferably made of a relatively hard plastic material, such as acrylic resin, polyvinyl chloride (PVC) or polyamide polymer, which can be formed into the desired shape by conventional molding or casting operations. If desired, the device may also be made out of metal, such as aluminum or stainless steel, by a suitable metal forming operation, e.g. casting or machining. In either case, the material selected should be one that can withstand repeated treatment by suitable sterilization media.

As noted above, the scale 25 facilitates the initial measurement and positioning of the second probe in arriving at the final measurement, after accounting for the factored distance. In the embodiment of FIG. 2, the scale 25 may be provided on the exterior of the rod-like body during the forming operation, or thereafter, by techniques such as engraving or etching.

The gauging device of FIG. 2 may include a stop means for maintaining the relative position of the probes 15 and 21 at any desired spacing on the rod-like body 13. To this end, the gauging device shown in FIG. 2 is provided with a set screw 27, which passes through the sleeve and frictionally engages the rod-like body. As can best be seen in FIG. 3, the rod-like body of the gauging device is preferably formed with a longitudinal groove or slot 29, in which the tip of the set screw 27 rests, in order to maintain the first and second probes in substantially parallel relationship.

A practical size of the gauging device of FIG. 2 has a rod-like body 11 which is about 1 cm in diameter and about 14 cm long, with one probe 15 approximately 3.5 cm in length adjacent one end thereof and a sleeve 17 which is about 4 cm long by about 2.5 cm in its widest dimension, with a passageway therethrough which is slightly larger than 1 cm in diameter. The second probe 21, also about 3.5 cm in length projects perpendicularly from the sleeve 17. A hole of about 0.3 cm is drilled through the wide dimension of the slide and is threaded for threadably receiving the set screw 27.

In this embodiment of the invention, the scale 25 has a single set of indicia calibrated to establish the actual distance between the probe tips 19 and 23. Alternatively, the scale may have dual sets of indicia, one of which establishes the initial measurement of the procedure and the other of which is correlated to the first set to establish the factored distance corresponding to the initial measurement on the first set of indicia, as the procedure is described more completely hereinafter.

FIG. 4 illustrates a forceps-like or scissor-type gauging device 30 for use in the present invention. This device comprises a pair of arms 31, 33, journalled on suitable pin means 35 intermediate their ends to allow displacement of the arms relative to one another about a pivotal axis concentric with the pin means. The first probe 37 is articulated adjacent one end of one arm 31 of the pair of arms and the second probe 41 is articulated on the corresponding end of the other arm 33 of the pair of arms, the arm ends on which the probes are mounted being disposed on the same side of the pivotal axis at 35, with the tips of the probes 39, 43 being parallel to one another. An arcuate scale 45 is provided which is centered on the pivotal axis at 35. In the gauging device of FIG. 4, the scale may be rigidly affixed to one of the arms, as shown, with the scale making frictional contact along its length with the other arm, in order to maintain any desired spacing between probes 37 and 41. Alternatively, the pin means 35 may be designed so that a threshold applied force must be exceeded before the arms may be displaced with respect to one another. Manufacturing techniques for a device such as that shown in FIG. 4 are well-known. Suitable materials for making a device of this kind include plastics and metals such as those mentioned above. Finger holes 47 may be provided on the end of each arm to facilitate manipulation of the device.

The method for determining vertical dimension of occlusion according to this invention is best described with reference to FIG. 1. In FIG. 1A, with the tip 23 of one probe in registry with the anterior wall of the auditory meatus, set screw 27 is loosened and the sleeve 17 is positioned so that the tip 19 of the other probe is in registry with the most lateral part of the orbit of the eye. The set screw is then tightened and a measurement, e.g. in millimeters, is taken from the indicia on the scale 25. Experience has shown that this measurement will generally range from 60 to 85 mm, depending on relative size of the cranium. Probe 21 is then positioned according to the factored distance, as set forth in Table A below, and set screw 27 is again tightened. The factored distances set forth in Table A have been empirically determined.

TABLE A

| First measurement | Factor | Factored Distance |
|---|---|---|
| 60 mm | −5.0 mm | 55.0 mm |
| 65 mm | −4.5 mm | 61.5 mm |
| 70 mm | −4.0 mm | 66 0 mm |
| 75 mm | −3 5 mm | 71.5 mm |
| 80 mm | −3.0 mm | 77.0 mm |

As the first measurement and corresponding factored distance set forth in Table A indicate, for each millimeter increment of the first measurement made between 60 and 80 mm, a deduction of 0.1 mm is made, from a high of 5 mm at a first measurement of 60 mm to a low of 3.0 mm at a first measurement of 80 mm. The first measurement, adjusted by the factor establishes the factored distance which equals the vertical distance between the nasal spine and most anterior part of the undersurface of the mandible, as shown in FIG. 1B, when the upper and lower teeth are occluded at normal vertical dimension. As indicated above, the factors of Table A may be incorporated in the scale by providing dual sets of indicia. The initial measure must register the probe 21 with the indicia of the first set, and when the probe is adjusted to establish the factored distance it may be accomplished by registering it with a correlated point on the second set of indicia.

The accuracy of the method of the invention was demonstrated in practice by performing occlusal vertical dimension determinations on 100 patients using a gauging device of the type shown in FIG. 2. Of the 100 patients on whom the method was performed, 70 were patients with no missing teeth (not including third molars). These patients had no complaints, signs or symptoms of an occlusal disorder. Twenty-six of the patients were missing from 1-4 teeth (not including third molars). Of the four remaining patients, two were completely endentulous in their upper jaws, with only six remaining lower anterior teeth and the other two were completely endentulous.

All but two of the 70 patients with no missing teeth corroborated the accuracy of the above method for determining normal vertical dimension of occlusion.

All of the 26 patients missing from 1-4 teeth had serious complaints of temporomandibular joint disorder, as well as signs and symptoms thereof. All were deficient in vertical dimension of occlusion from 3-8 mm, according to the method of the invention. All were fitted with appliances to restore normal jaw position and vertical dimension of occlusion. All responded well to this treatment and adjustments of appliances were much fewer, as compared to previous therapies using appliances fitted based upon previously proposed methods for establishing vertical dimension.

In treating the four patients (two endentulous in the upper jaw and 2 completely endentulous) the method of the invention was used to record the vertical dimension of occlusion. All four patients were successfully fitted with dentures and necessary adjustments were minimal.

While the various aspects of the present invention have been described and exemplified above in terms of certain preferred embodiments, various other embodiments may be apparent to those skilled in the art. For example, as empirical data is accumulated, the data in Table A may be expanded or may be incorporated in an automated instrument which has the necessary data in its memory to indicate the proper factored distance corresponding to any initial measurement. The invention is, therefore, not limited to the embodiments specifically described and exemplified, but is capable of variation and modification without departing from the spirit and scope of the appended claims.

What is claimed is:

1. A method for determining vertical dimension of occlusion comprising the steps of:

providing a gauging device comprising a first probe terminating in a first tip portion affording registry of said first tip with selected anatomical parts, and a second probe adjustably mounted substantially parallel to said first probe for adjustment relative to said first probe and said second probe having a second tip portion affording registry of said second tip with selected anatomical parts;

first registering one of said tips with the external auditory meatus, and adjusting said gauging device to register the other of said tips with the lateral corner of the ocular orbit to establish a first measurement;

then positioning the tip of the second probe spaced relative to the tip of said first probe a factored distance based on said first measurement;

thereafter, without changing said positioning of the tips, registering one of said tips with the nasal spine and positioning the other of said tips adjacent the anterior part of the undersurface of the mandible; and then positioning the mandible to engage said other tip.

2. A method as claimed in claim 1, including providing a scale on said gauging device having at least one set of indicia for establishing said first measurement, and providing means to establish said factored distance based on the measurement established by the indicia of said scale.

3. A method as claimed in claim 2, wherein said gauging device comprises an elongated rod-like body having an elongated axis, said first probe being disposed adjacent one end of said body projecting transversely from said axis, and a slide axially adjustable on said rod-like body, said second probe being disposed on and projecting from said slide substantially parallel to said first probe, said scale being disposed longitudinally along said rod-like body, and having its indicia in the path of adjustment of said slide, said adjusting step comprising displacing said slide on said rod and establishing said first measurement by registration with the indicia said scale.

4. A method as claimed in claim 2, wherein said gauging device comprises a pair of arms movably connected intermediate their ends to allow displacement of said arms relative to one another about a pivotal axis, said first probe being articulated on an end of one of said pair of arms and said second probe being articulated on an end of the other of said pair of arms, the arm ends on which said probes are mounted being disposed on the same side of said pivotal axis, the tips of said first probe and said second probe being parallel to each other, and an arcuate scale centered on said pivotal axis, said adjusting step comprising displacing said arms relative to one another and establishing said first measurement by registration with the indicia of said scale.

5. A method as claimed in claim 2, wherein the means to establish said factored distance is Table A of the specification.

6. A method as claimed in claim 1, wherein the first measurement is the distance between said probe tips and the factored distance to which the tip of the second probe is positioned is as set forth in Table A of the specification.

* * * * *